United States Patent [19] [11] 4,128,727
Leupold et al. [45] Dec. 5, 1978

[54] PROCESS FOR THE MANUFACTURE OF ACETIC ACID ETHYL ESTER

[75] Inventors: Ernst I. Leupold, Westerfeld; Hans-Jürgen Arpe, Fischbach, Taunus; Albert Renken, Hofheim, Taunus; Ernst-Günther Schlosser, Kelkheim, all of Fed. Rep. of Germany

[73] Assignee: Hoechst Aktiengesellschaft, Frankfurt am Main, Fed. Rep. of Germany

[21] Appl. No.: 859,534

[22] Filed: Dec. 12, 1977

Related U.S. Application Data

[63] Continuation of Ser. No. 731,767, Oct. 12, 1976, abandoned.

[30] Foreign Application Priority Data

Oct. 14, 1975 [DE] Fed. Rep. of Germany ....... 2545845

[51] Int. Cl.$^2$ .............................................. C07C 67/05
[52] U.S. Cl. .................................................... 560/247
[58] Field of Search ......................................... 560/247

[56] References Cited

U.S. PATENT DOCUMENTS

| | | | |
|---|---|---|---|
| 1,365,052 | 1/1921 | Ellis | 560/247 |
| 2,224,809 | 12/1940 | Coleman | 560/247 |
| 2,741,632 | 4/1956 | Cottle | 560/247 |
| 3,474,131 | 10/1969 | Schmerling | 560/247 |
| 3,922,294 | 11/1975 | Lewpold | 560/247 |

Primary Examiner—James O. Thomas, Jr.
Assistant Examiner—Michael Shippen
Attorney, Agent, or Firm—Curtis, Morris & Safford

[57] ABSTRACT

Acetic acid ethyl ester is prepared by passing ethylene over a fixed-bed catalyst composed of silicon dioxide, which has a surface from 50 to 200 m$^2$/g and which is impregnated with H$_2$SO$_4$, diethylsulfate or ethylsulfuric acid or mixtures of these compounds, with periodically alternating quantities of acetic acid, at a temperature from 130° to 170° C, the acid concentration, calculated on ethylene, varying constantly over a range from 0.01 to 40% by mole.

12 Claims, No Drawings

PROCESS FOR THE MANUFACTURE OF ACETIC ACID ETHYL ESTER

This is a continuation, of application Ser. No. 731,767 filed Oct. 12 1976, now abondoned.

The present invention relates to a process for the continuous manufacture of acetic acid ester by addition of acetic acid to ethylene.

It is known to react acetic acid in the presence of acidic catalysts with ethylene to yield acetic acid ethyl ester. In the literature several proposals have been made concerning the catalysts and the operation methods. A summary of these proposals has been published by Y. Murakami, T. Hattori and H. Uchida in J. Chem. Soc. Japan, Ind. Chem. Sect. (Kogyo Kagaku Zasshi) 72 (9), 1945–1948 (1969). It can be seen therefrom that catalysts containing oxides of chromium, molybdenum and tungsten in the form of different heteropoly acids, which are used for the catalysis in the gaseous phase, show a certain initial activity at relatively high temperature of more than 200° C. and under a pressure of up to 150 bars, but become nearly inactive after a few hours. Catalysts containing phosphoric acid, $H_3PO_4$, when used for the reaction in a gaseous phase are unsuitable because of their low activity. Acidic ion exchange resins cannot be used owing to their instability at temperatures even below the required reaction temperature.

Considerable difficulties also arise when performing the reaction in the liquid phase. For this reason a portion of 67% of a sulfuric acid of 96% strength, calculated on acetic acid to be reacted, for example, has been proposed in the reaction zone, for the manufacture of acetic acid ethyl ester from acetic acid and ethylene.

It is, however, known that high concentrations of mineral acids lead to a partial polymerization of ethylene and, consequently, to losses of ehtylene and to polymer by-products, which can only be removed with difficulties from the catalyst solution. A further substantial disadvantage of mineral acids of high concentration resides in the fact that they bring about considerable corrosion problems, which hinder their use on an industrial scale.

As a summary it can be said that none of the methods proposed in the literature has proved appropriate for an economic manufacture of acetic acid esters on an industrial scale.

The present invention consequently provides a process for the manufacture of acetic acid ethyl ester by reaction of acetic acid and ethylene in the gaseous phase in the presence of acidic catalysts, which comprises passing ethylene over a fixed-bed catalyst with periodically alternating quantities of acetic acid at a temperature from 130° to 170° C., the catalyst being composed of silicon dioxide, which has a surface from 50 to 200 $m^2/g$ and is impregnated with $H_2SO_4$ or diethyl sulfate or ethylsulfate acid or mixtures of these compounds, the acetic acid concentration, calculated on ethylene, varying constantly over a range from 0.01 to 40% by mole.

The process according to the invention has surprisingly decisive advantages as compared to the previously proposed methods. One advantage resides in the fact that the efficiency of the catalyst according to the invention is nearly unchanged under the reaction conditions even after more than 1000 hours. Another advantage resides in the fact that there are practically no losses of ethylene due to polymerization. A formation of by-products or undesired consecutive products can not at all be observed.

The process according to the invention can be performed in the following manner generally: Ethylene and acetic acid in a gaseous state are passed through a reaction zone in a reactor, in which the catalyst is arranged as a fixed-bed. In this process acetic acid may either be passed over a pre-evaporator or be introduced directly to the reaction zone, where it vaporizes immediately under the reaction conditions.

A heatable tube, which may be made of glass or stainless steel, for example, may serve as a reaction zone, in which the catalyst is arranged as a fixed-bed. Other reactor forms and materials may also be used, however.

The reaction temperature is in the range from 130° to 170° C., preferably from 140° to 150° C., slightly higher or lower temperatures being also possible.

A pressure range from 0.5 to 10 bars is suitable for the process according to the invention, but higher pressures, for example up to 100 bars, may also be applied without difficulty.

The service life of the catalyst as well as the space-time-yield of the catalyst in the process of the invention is defined in characteristic manner by the acetic acid concentration in the reactor. The permanent variation of the acetic acid concentration in the reactor is in a range between a minimum value and a maximum value from 0.01 to 40% by mole, calculated on ethylene, and is particularly advantageously achieved in definite intervals.

This permanent variation may be achieved most easily, for example, by continuously regulating the acetic acid admission in periods, during which acid is added and during which the addition is dicontinued by means of a time switcher.

The duration of these intervals with or without acid addition depends substantially on the desorption velocity of the acetic acid from the catalyst under the reaction conditions. As acetic acid is absorbed by the catalyst to a higher degree than ethylene, the catalytically active surface of the catalyst would be substantially covered with acetic acid alone after a short period of time, when working without interruption of the acetic acid addition, and as a consequence thereof only a very small part of ethylene would be activated, thus considerably reducing the ester formation velocity. In practice the invention may also be advantageously operated in the following manner: Acetic acid is introduced into the reactor during an intervals from 2 to 60 minutes, for example, preferably 5 to 30 minutes, and the addition is then interrupted for 0.1 to 15 minutes, preferably 1 to 10 minutes, while ethylene is added without interruption. As a consequence of such a repeated discontinuance of the acetic acid addition a part of the acetic acid absorbed by the catalyst is desorbed again and again so that a sufficient quantity of ethylene is likewise absorbed generally.

$SiO_2$ used for the manufacture of the catalyst has a specific surface from 50 to 200 $m^2/g$, preferably from 80 to 170 $m^2/g$. Considerably larger or smaller surfaces may lead to noticeably reduced yields of acetic acid ethyl ester.

The catalyst may generally be prepared in the following manner: $SiO_2$ is impregnated with $H_2SO_4$ and/or diethylsulfate or ethylsulfuric acid or with mixtures of these compounds, preferably in admixture with acetic acid, and dried subsequently under a reduced pressure at a temperature of about 140° C. Among the catalysts prepared in said manner there are preferably used those having a content of $H_2SO_4$ and/or diethylsulfate and/or ethylsulfuric acid or mixtures of these compounds from about 10 to 30% by weight, optionally after removal of the acetic acid by drying.

If the material load of the catalyst is too high during the reaction a small discharge and, consequently, losses of the impregation may occur whereby the space-time-yield of the catalyst may be slightly reduced in the course of several hundred hours. In such cases it has proved advantageous to introduce $H_2SO_4$ and/or diethylsulfate and/or ethylsulfuric acid dissolved in acetic acid into the reactor together with the reaction components in an amount from about 0.1 to about 2% by weight, calculated on the acetic acid introduced into the reactor.

The reaction product may be worked up continuously or discontinuously by applying the known methods. The preferred method consists in separating the reaction mixture continuously while isolating pure acetic acid ethyl ester. For this purpose the reaction mixture is cooled after having left the reactor, whereby ethylacetate and non-converted acetic acid condense, whereas non-converted ethylene is separated in a gaseous state and recycled to the reactor. The condensate is preferably continuously submitted to a fractionated distillation, whereby non converted acetic acid is recovered from the bottom product of the distillation column and recycled to the reactor, whereas pure acetic acid ethyl ester is obtained at the top of the column.

The selectivity of the process according to the invention is extremely high; it is nearly 100%, referring to acetic acid as well as to ethylene.

Acetic acid ethyl ester is used to a considerable extent, for example, as a solvent for lacquers and adhesives.

The following examples illustrate the invention:

EXAMPLES 1 TO 3

A total of 10 ml/h of acetic acid is introduced by pumping alternatingly by means of a dosage pump, while simultaneously adding 20 Nl/h of ethylene, at the top of a vertically arranged glass tube reactor of 30 cm length and 100 ml volume, which is filled with about 100 ml of a catalyst composed of $SiO_2$, impregnated with 25% by weight of $H_2SO_4$ and having a certain surface as indicated in Table 1 and which is heated to a temperature of 138° C., the acetic acid addition being interrupted constantly for 2 minutes after 6 minutes. The reaction mixture leaving the reactor is brought to normal temperature, liberated from excess ethylene and analysed. It contains besides non-converted acetic acid only acetic acid ethyl ester so that the selectivities calculated on converted ethylene as well as on converted acetic acid are practically 100%. Table 1 indicated the content of acetic acid ethyl ester in the reaction mixture liberated from ethylene of the Examples 1 to 3. The non-converted portions of ethylene and acetic acid may be recylced to the reactor without particular purifying operations.

TABLE I

Influence of the catalyst surface on the conversion

| Example | $SiO_2$-surface ($m^2/g$) | % by weight of acetic acid ethyl ester in the reaction mixture |
|---|---|---|
| 1 | 110 | 34.2 |
| 2 | 120 | 60.0 |
| 3 | 160 | 37.4 |

COMPARATIVE EXAMPLES 1 AND 2

The invention is operated in the same manner as in Examples 1 to 3, except that comparable catalysts are used having a $SiO_2$ surface other than that according to the invention. Table 2 shows the results obtained. The portions of acetic acid ethyl ester in the reaction mixture are noticeably smaller.

TABLE II

Influence of the catalyst surface on the conversion

| Comparative Example | $SiO_2$-surface ($m^2/g$) | % by weight of acetic acid ethyl ester in the reaction mixture |
|---|---|---|
| 1 | 0.6 | 14.6 |
| 2 | 350 | 10.0 |

EXAMPLE 4 TO 7

The apparatus described in the Examples 1 to 3 is filled each time with 100 ml of a catalyst (carrier: $SiO_2$ having a surface of 120 $m^2/g$) provided with the impregnation indicated in Table 3 and fed with ethylene and acetic acid in an analogous manner to Examples 1 to 3. The reaction temperature in the reactor is 144° C. Table 3 indicated the portions of acetic acid ethyl ester in the reaction mixture.

The selectivities, calculated on converted acetic acid as well as on converted ethylene, in the Examples 4 to 7 are 100%.

TABLE III

Influence of the catalyst impregnation on the conversion

| Example | Impregnation by weight (each time 20 % by weight) | % by weight of acetic acid ethyl ester in the reaction mixture |
|---|---|---|
| 4 | $H_2SO_4$ | 61.5 |
| 5 | diethylsulfate | 59.2 |
| 6 | ethylsulfuric acid | 59.7 |
| 7 | $H_2SO_4$ / diethylsulfate 1 : 1 | 60.4 |

EXAMPLES 8 TO 10

800 Nl/h of ethylene as well as alternatingly acetic acid having a content of diethylsulfate of 0.7% by weight are introduced continuously at the top of a vertically arranged V4A-stainless steel reactor of 100 cm length, which is filled with 250 ml of catalyst ($SiO_2$, 120 $m^2/g$, 25% by weight of diethylsulfate), at a temperature of 147° C. The alternating acetic acid addition is carried out in the following manner: The addition is interrupted each time for one interval after 5 dosing intervals. A total of 150 ml/h of acetic acid is metered into the reactor. The pressure in the reactor is 6 bars. The reaction mixture leaving the reactor is worked up continuously. The excess ethylene is recycled to the reactor. The portion of the reaction mixture liquid at normal temperature is fractionated in a distillation column. The acetic acid ethyl ester is withdrawn at the top of the column. A mixture containing besides small quantities of acetic acid ethyl ester unconverted acetic acid is recycled to the reactor continuously from the bottom. Table 4 indicates the different intervals of the alternating acetic acid addition of the Examples 8 to 10 as well as the space-time-yields obtained. The selectivities for acetic acid ethyl ester, calculated on converted ethylene and converted acetic acid, are in all cases 100%.

TABLE IV

| Example | Intervals of the acetic acid addition (min) addition | Intervals of the acetic acid addition (min) without addition | Space-time-yield of the acetic acid ethyl ester formation (g/l.h) |
| --- | --- | --- | --- |
| 8 | 5 | 1 | 205 |
| 9 | 12.5 | 2.5 | 178 |
| 10 | 25 | 5 | 164 |

The same values for the space-time-yield of the acetic acid ethyl ester formation as well as the same selectivities are obtained even after a continuous operation time of more than 1000 hours.

COMPARATIVE EXAMPLE 3

When operating in the same manner as in the Examples 8 to 10, except that the acetic acid addition is not performed alternatingly, but that 150 ml/h of acetic acid are added without interruption, the space-time-yield of the acetic acid ethyl ester formation is only 100 g/l. h.

What is claimed is:

1. In a process for the manufacture of acetic acid ethyl ester by reaction of acetic acid and ethylene in the gaseous phase in the presence of an acidic catalyst, the improvement which comprises passing ethylene and acetic acid over a fixed-bed catalyst at a temperature of from 130° to 170° C., the catalyst being composed of silicon dioxide having a surface area of from 50 to 200 m$^2$/g and being impregnated with H$_2$SO$_4$, diethylsulfate or ethylsulfuric acid, or a mixture thereof, the acetic acid concentration, calculated on ethylene, uninterruptedly varying over a range of from 0.01 to 40% by mole.

2. The process as defined in claim 1, wherein the acetic acid ethyl ester is continuously separated from the reaction mixture and the non-converted portions of acetic acid and ethylene are recycled to the reactor.

3. The process as defined in claim 1, wherein losses of H$_2$SO$_4$, diethylsulfate, ethylsulfuric acid, or a mixture thereof, in the catalyst are recovered.

4. The process as defined in claim 1, wherein the acetic acid concentration varies over a range of from 0.1 to 30% by mole.

5. The process as defined in claim 1, wherein the amount of acetic acid added varies periodically.

6. The process as defined in claim 1, wherein the temperature is from 140° to 150° C.

7. The process as defined in claim 1, wherein the silicon dioxide has a surface area of from 80 to 170 m$^2$/g.

8. The process as defined in claim 1, which comprises adding acetic acid discontinuously by interrupting the addition at regular intervals.

9. The process as defined in claim 8, wherein the acetic acid is added during intervals of from 2 to 60 minutes, 0.1 to 15 minutes passing between the end of an addition interval and the beginning of the succeeding interval.

10. The process as defined in claim 9, wherein said intervals are of from 5 to 30 minutes.

11. The process as defined in claim 9, wherein 1 to 10 minutes passes between the end of an additional interval and the beginning of the succeeding interval.

12. The process as defined in claim 11, wherein said intervals are of from 5 to 30 minutes.

* * * * *